(12) United States Patent
Chien (10) Patent No.: US 9,233,999 B2
(45) Date of Patent: Jan. 12, 2016

(54) RECOMBINANT PROTEIN, PHARMACEUTICAL COMPOSITION CONTAINING THE SAME, AND METHOD OF BIOSYNTHESIZING

(71) Applicant: Hung-Chien Chien, Taichung (TW)

(72) Inventor: Hung-Chien Chien, Taichung (TW)

( * ) Notice: Subject to any disclaimer, the term of this patent is extended or adjusted under 35 U.S.C. 154(b) by 57 days.

(21) Appl. No.: 14/023,537

(22) Filed: Sep. 11, 2013

(65) Prior Publication Data
US 2014/0186429 A1 Jul. 3, 2014

(30) Foreign Application Priority Data
Dec. 28, 2012 (TW) .............................. 101151237 A (51) Int. Cl.
*A61K 38/00* (2006.01)
*A61K 38/03* (2006.01)
*C07K 2/00* (2006.01)
*C12N 9/02* (2006.01)

(52) U.S. Cl.
CPC ................ *C07K 2/00* (2013.01); *C12N 9/0071* (2013.01); *C12Y 114/16002* (2013.01)

(58) Field of Classification Search
CPC ............................... A61K 38/00; A61K 38/03
USPC .......................................................... 435/183
See application file for complete search history.

(56) References Cited

FOREIGN PATENT DOCUMENTS

TW 1315341 B 10/2009

*Primary Examiner* — Maryam Monshipouri
(74) *Attorney, Agent, or Firm* — Bacon & Thomas, PLLC (57) ABSTRACT

The present invention provides a method of biosynthesizing a recombinant protein containing the biologically active peptide, the pharmaceutical composition containing the recombinant protein as well as the preparation of the recombinant protein. Simply speaking the consecutively multiple copies of the bioactive peptide are replaced in the amino acid sequence of a recombinant protein (so called peptide-protein). Then, a high concentration and high yield of the peptide-protein containing the consecutively multiple copies of the bioactive peptide is produced by the biosafety and edible strain of yeast without any endotoxin contamination.

7 Claims, 7 Drawing Sheets

```
                           overlapping region
        F  G   H  K   F   G   H   K   F   G  H  K  F
                   AAA TTT GGA CAT AAA TTT GGCCACAAGTTC
        AAGCCGGTA TTT AAA CCT GTA TT
```

Forward primer 3F : 5' - AAATTTGGACATAAATTTGGCCACAAGTTC-3'
Reverse primer 3R : 5' - TTATGTCCAAATTTATGGCCG AA-3'

```
                                overlapping region
        F G H K  F   G   H   K   F   G   H   K   F  G  H  K  F
                    GGA CAT AAA TTT GGA CAT AAA TTCGGCCACAAGTTC
        AAGCCGGTGTTCAAG CCT GTA TTT AAA CCT GTA TTT AAG
```

Forward primer 4F : 5' - GGACATAAATTTGGACATAAATTCGGCCACAAGTTC-3'
Reverse primer 4R : 5' - GTCCAAATTTATGTCCGAACTTGTGGCCGAA-3'

```
        F G H K F G   H   K   F   G   H   K   F    G H K F G H K F
                    GGA CAT AAA TTT GGA CAT AAA TTCGGCCACAAGTTCGGCCACAAGTTC
        AAGCCGGTGTTCAAG CCT GTA TTT AAA CCT GTA TT
```

Forward primer 5F : 5' - AAATTTGGACATAAATTTGGCCACAAGTTCGGCCACAAGTTC-3'
Reverse primer 5R : 5' - TTATGTCCAAATTTATGTCCGAACTTGTGGCCGAA-3'

FIG. 1

| | | | |
|---|---|---|---|
| Original design | 1 | 1 MPTPDATTPQAKGFRRAVSRYLGYLEQLLRYLGYLEQLLRYLGYLEQLLRYLGYLEQLLRYL | 62 Domain I |
| Clone | 2 | 1 MPTPDATTPQAKGFRRAISRYLGYLEQLLRYLGYLEQLLRYLGYLEQLLRYLGYLEQLLRYL | 62 |
| Original design | 1 | 63 GYLEQLLRVAFEEEGKRYLGYLEQLLRYLGYLEQLLRYLGYLEQLLRYLGYLEQLLRYLGY | 124 Domain II |
| Clone | 2 | 63 GYLEQLLRVAFEEEGKRYLGYLEQLLRYLGYLEQLLRYLGYLEQLLRYLGYLEQLLRYLGY | 124 |
| Original design | 1 | 125 LEQLLRFYRLEVRRGRYLGYLEQLLRYLGYLEQLLRYLGYLEQLLRYLGYLEQLLRYLGYLE | 186 Domain III |
| Clone | 2 | 125 LEQLLREVRLEVRRGRYLGYLEQLLRYLGYLEQLLRYLGYLEQLLRYLGYLEQLLRYLGYLE | 186 |
| Original design | 1 | 187 QLLRHPGFSDQYTRYLGYLEQLLRYLGYLEQLLRYLGYLEQLLRYLGYLEQLLRYLGYLEQL | 248 Domain IV |
| Clone | 2 | 187 QLLRHPGFSDQYYRYLGYLEQLLRYLGYLEQLLRYLGYLEQLLRYLGYLEQLLRYLGYLEQL | 248 |
| Original design | 1 | 249 LRHLEAFALLERYLGYLEQLLRYLGYLEQLLRYLGYLEQLLRYLGYLEQLLRYLGYLEQLLR | 310 Domain V |
| Clone | 2 | 249 LRHLEAFALLERYLGYLEQLLRYLGYLEQLLRYLGYLEQLLRYLGYLEQLLRYLGYLEQLLR | 310 |
| Original design | 1 | 311 TQYIRHASSPMHSPEPDCCHELLGHVPMLADRTFAQFSQDIGLASLGASDEEIEKLSTLYWF | 372 Starch |
| Clone | 2 | 311 TQYIRHASSPMHSPEPDCCHELLGHVPMLADRTFAQFSQDIGLASLGASDEEIEKLSTLYWF | 372 binding Domain |
| Original design | 1 | 373 TVEFGLCKQNGEVKAYGAGLLSSYGEELHCESEEPEIRAFDPEAAVQPYQDQTYQSVYFVS | 434 |
| Clone | 2 | 373 TVEFGLCKQNGEVKAYGAGLLSSYGEELHCLSEEPEIRAFDPEAAVQPYQDQTYQSVYFVS | 434 |
| Original design | 1 | 435 ESFSDAKDKLRSYASRIQRPFSVKFDPYTLAIDVLDSPQAVRRSLEGVQDEDTLAHALSAI | 496 |
| Clone | 2 | 435 ESFSDAKDKLRSYASRIQRPFSVKFDPYTLAIDVLDSPQAVRRSLEGVQDEDTLAHALSAI | 496 |
| Original design | 1 | 497 G 497 |
| Clone | 2 | 497 G 497 |

RECOMBINANT PROTEIN, PHARMACEUTICAL COMPOSITION CONTAINING THE SAME, AND METHOD OF BIOSYNTHESIZING

BACKGROUND OF THE INVENTION

1. Field of the Invention

This invention discloses a recombinant protein, especially a recombinant protein containing the biologically active peptide, a pharmaceutical composition containing the same and a method of biosynthesizing thereof.

2. Description of the Related Art

Among the peptide, amino acid and protein, the molecular weight of peptide is between amino acid and protein Amino acid is the basic unit with least molecule weight in the protein, and protein is largest molecule assembled by one or multiple peptide chains. The peptide chain is accomplished by formation of the peptide bond from two or more amino acids with loss of the water molecule. After the peptide chains formation, these multiple peptide chains further assemble into protein through dehydroxylation. On the other hand, protease mediated proteolysis breakdowns the protein into multiple peptide chains with molecular size in nanometer scale. Therefore, peptide in nanometer scale is tent to be absorbed by intestines, stomach, blood vessels and skin.

Peptides include the nutritional peptides and functional peptides according to their functions. Nutritional peptides are the source of amino acids for animals and human beings. Functional peptides, the bioactive peptides, exhibit specific physiological activity in animals and human beings and have wide application.

So far, production of the bioactive peptides is by using protease-mediated proteolysis from edible protein or directly synthesizing by ligation of amino acids when the bioactive peptide comprising less than five amino acid residues.

However, these methods of bioactive peptides have low yield and elevate the manufacturing cost, therefore limit the peptide synthesis in industrial scale. Due to the concern of cost and price, the concentration of bioactive peptides applied in drugs, health foods and cosmetics rarely reach the optimized concentration. So the bioactive peptides applied in these products are unable to exhibit claimed function for preventing or curing the targeted diseases while consumers take these products.

Actually, these applied bioactive peptides are functional in the experiment of selection or animal tests, but fail to reveal the same in commercial products for consumers. One reason of functional deficiency lies on low concentration of bioactive peptides in the commercial product. The other reason is the orally taken bioactive peptides contained in products are destroyed by various proteases in digestion tract.

Previous patent, Taiwan Patent No. I315341, filed by the applicant had disclosed a method for biosynthesizing the VVVP peptide-protein producing with edible bacterium utilizing single copy insertion of said peptide into each replacement region within the carrier protein α-amylase. But the expression vector comprises six replacement regions and each of them is inserted with single copy of bioactive peptide and the carrier protein is purified from Ni-NTA purification system. Therefore, the ratio of the bioactive peptides in the protein product is only 3% which is too low for commercial production and the protein product may contain heavy metal nick which is toxic for human body.

Collectively, the improvement of producing yield of the bioactive peptides and increasing of the bioactive peptide concentration in final protein product come to be a critical issue in the field of peptides production.

SUMMARY OF THE INVENTION

Therefore, there is a purpose of this present invention to provide a recombinant protein, pharmaceutical composition containing the recombinant protein and method of biosynthesizing the recombinant protein to massive express the bioactive peptide for high concentration and high yield with less manufacturing cost.

In order to achieve this purpose, one embodiment of this present invention provides a recombinant protein comprising at least one region having consecutively multiple copies of bioactive peptides. Therefore, it can produce consecutively multiple copies of the bioactive peptides by substituting into the recombinant protein to achieve high yield, high concentration and low cost.

Another example of said recombinant protein, wherein each said bioactive peptide is selected from the group consisting of GHK, SEQ ID NO: 2, 3, 4, 5 to reveal biological function.

Another example of said recombinant protein provides a cutting site of pepsin, trypsin or carboxypeptidase B to protect both ends of the bioactive peptides and to let the bioactive peptides can be specifically cut, released and absorbed to express its function.

In order to achieve this purpose, another embodiment of this present invention provides a pharmaceutical composition comprising at least one region having consecutively multiple copies of bioactive peptides into the recombinant protein for pharmaceutical applications.

Another example of said pharmaceutical composition, wherein each said bioactive peptide is selected from the group consisting of GHK, SEQ ID NO: 2, 3, 4, 5 to reveal biological function.

Another example of said pharmaceutical composition provides a cutting site of pepsin, trypsin or carboxypeptidase B to protect both ends of the bioactive peptides and to let the bioactive peptides can be specifically cut, released and absorbed to express its function.

Another example of said pharmaceutical composition, the form of the pharmaceutical composition could be selected from the group consisting of emulsion, electuary, gel, lotion, mash, oil soluble concentrate, softener, liposome, nanoparticle, toning lotion, mouthwash, shampoo, milky lotion, spray, suppository, capsule, pastille, powder, syrup, particulate matter, solution, suspension, paste or masking paste.

In order to achieve this purposes, another embodiment of this present invention provides a method of biosynthesizing recombinant protein, comprising the steps of providing a protein having at least one replacement region and a starch binding region; substituting said replacement region with a region having consecutively multiple copies of bioactive peptides; transforming said substituted protein to an expression system for fermentation; and purifying said substituted protein with starch. Therefore, it can produce consecutively multiple copies of the bioactive peptides by substituting into the recombinant protein to achieve high yield, high concentration and low cost.

Another example of said pharmaceutical composition, wherein each said bioactive peptide is selected from the group consisting of GHK, SEQ ID NO: 2, 3, 4, 5 to reveal biological function.

Another example of said method, the recombinant protein is human tyrosine hydroxylase.

Another example of said method, strain of the yeast is *Yarrowia lipolytica* to achieve the effect of biosafety, toxin-free and edible.

Another example of said method further comprising steps of selecting an overlap region with about 5~7 amino acids from central of said region having consecutively multiple copies of bioactive peptides; setting said 5~7 amino acid residues a DNA codon which is different from the same amino acid residues out of said overlap region; designing a forward primer and a reverse primer according to said nucleotide sequence which have different DNA codons and said forward primer and said reverse primer having about 12~20 complementary nucleotides at said overlap region; synthesizing two complementary sequence of DNA fragment coding for consecutively multiple copies of bioactive peptide utilizing polymerase chain reaction; and linking said each two replacement regions utilizing overlapping polymerase chain reaction.

The details about structure, features, assembling or utilizing method of this present invention will further explain in following text. However, above-mentioned specification is only for detailed description with the embodiment of this present invention and shall not be construed as a scope limitation of this present invention.

DETAILED DESCRIPTION OF THE INVENTION

The following examples and experiments with illustration of figures are utilized for description of the technical context and feature of this invention.

Example 1

Selection of the Carrier Protein

The best choice of the carrier protein is the protein from human body because it is easy to be produced from the endotoxin-free, biosafety and edible strain of yeast in large scale. Furthermore, the carrier protein must contain amylose-binding domain for purification by binding with edible cornstarch.

Previous reports show that human tyrosine hydroxylase (HTH) expressed in the endotoxin-free, biosafety and edible strain of yeast exhibits the greatest and most stable yield. Expression of target protein by using HTH as carrier can produce more than 200 gram peptide protein from 1 liter fermentation medium mixture. In contrast, *Aspergillus oryzae* expression system utilizing α-amylase as carrier protein acquires only 25 gram peptide protein from 1 liter fermentation medium mixture.

HTH is utilized as a major embodiment in this invention, which contains 497 amino acid residues (NCBI accession number AA43612, SEQ ID NO: 1). There is a fixed region of HTH, which cannot be substituted, with 183 amino acid residues comprising 1~20 amino acid residues at N-terminal domain and 314~477 amino acid residues at amylose-binding domain. The other 314 amino acid residues are designed for replacement by the expressed bioactive peptides which contain five replacement regions at 21~70, 81~130, 141~190, 201~250 and 261~310 amino acid residues.

Example 2

Substitution of Consecutively Multiple Copies of the Bioactive Peptide into the Expression Vector The expressed bioactive peptides are further substituted into the five indicated replacement regions in said carrier protein. The number of amino acid residues in each replacement regions is about 50 because of currently identified bioactive peptides usually less than 50 amino acids. Between each replacement regions, 10 original amino acids in said carrier protein were linked with the replacement regions.

314 amino acid residues in said carrier protein include five replacement regions and four original regions. Each replacement regions contain about 50 amino acid residues, and said original region comprises the 10 original amino acid residues. Taking a bioactive peptide with 10 amino acids for example, each replacement region is capable to substitute consecutively 5 copies of said bioactive peptides and there are total 25 said bioactive peptides within 5 replacement regions in said carrier protein. Therefore, expression of one said carrier protein containing 25 copies of said bioactive peptide could elevate 25 folds in concentration with comparison of current method with protein hydrolysis from the edible protein.

1. Preparation of Consecutively Multiple Copies of Bioactive Peptide

A hair follicle growth-induction peptide with amino acid sequence GHK is present as an example to describe the preparation process of consecutively multiple copies of bioactive peptide that each replacement regions can be replaced into 12 consecutively copies of said peptide.

Figure 1:
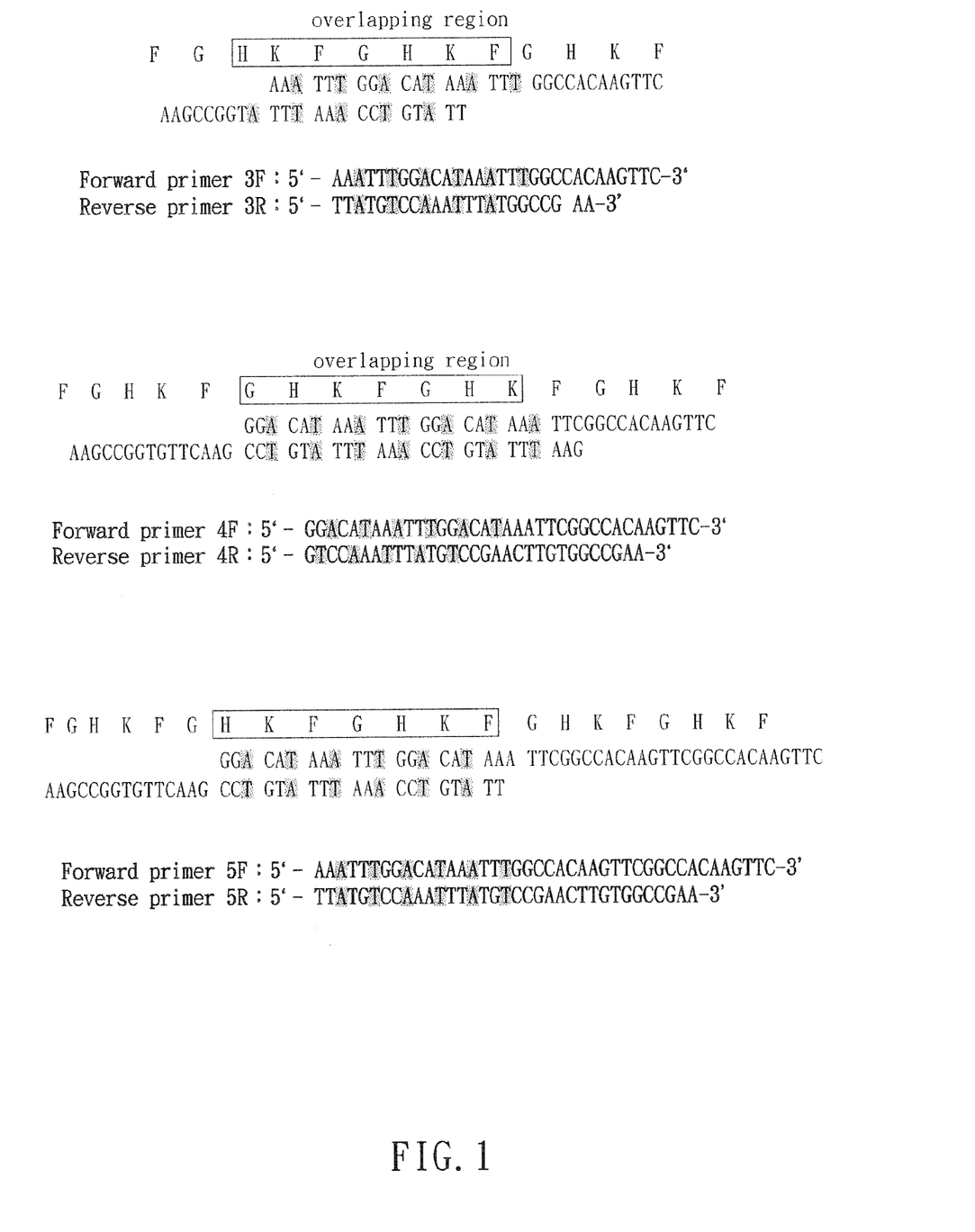
FIG. 1 is the illustration demonstrating consecutively multiple copies of the bioactive peptide.

FIG. 1 shows examples for synthesizing consecutively 3, 4, or 5 copies of bioactive peptide. First, to select 5~7 amino acid residues at central region of overlapping region wherein said selected amino acid residues have different DNA codon to the same amino acid residues out of said overlapping region and the forward and reverse primer are designed to have 12~20 complementary oligonucleotides within said overlapping region after translation. After that, to synthesis the forward and reverse primers and amplify DNA fragment coding for consecutively multiple copies of bioactive peptide by polymerase chain reaction (PCR). Finally, to link said multiple copies by overlap-PCR to get the consecutively 3, 4 or 5 copies of bioactive peptide. During said process, the setup of said overlapping region which contains 5~7 amino acids in central of the replacement region is most critical for the replication of consecutively multiple copies of bioactive peptide without loss of copy number.

Another example is the substitution of sleep-inducing peptide with amino acid sequence YLGYLEQLLR (SEQ ID NO: 2) into the carrier protein. To prepare a peptide having consecutively 5 copy of bioactive peptide by above mentioned process. Then, to synthesis nucleic acid sequence according to said peptide sequence and sequentially link 5 replacement regions and 4 original regions by overlap-PCR. In this process, every substitution of the replacement region was verified by DNA sequence. After that, to clone the final nucleotide sequence which encodes said recombinant protein containing the bioactive peptide (hereinafter referred to as the "peptide-protein") into the yeast secretory expression vector for expression and secretion of the peptide-protein and transform to the 5S-rDNA loci on the chromosome of the biosafety and edible yeast strain for fermentation.

Figure 2:
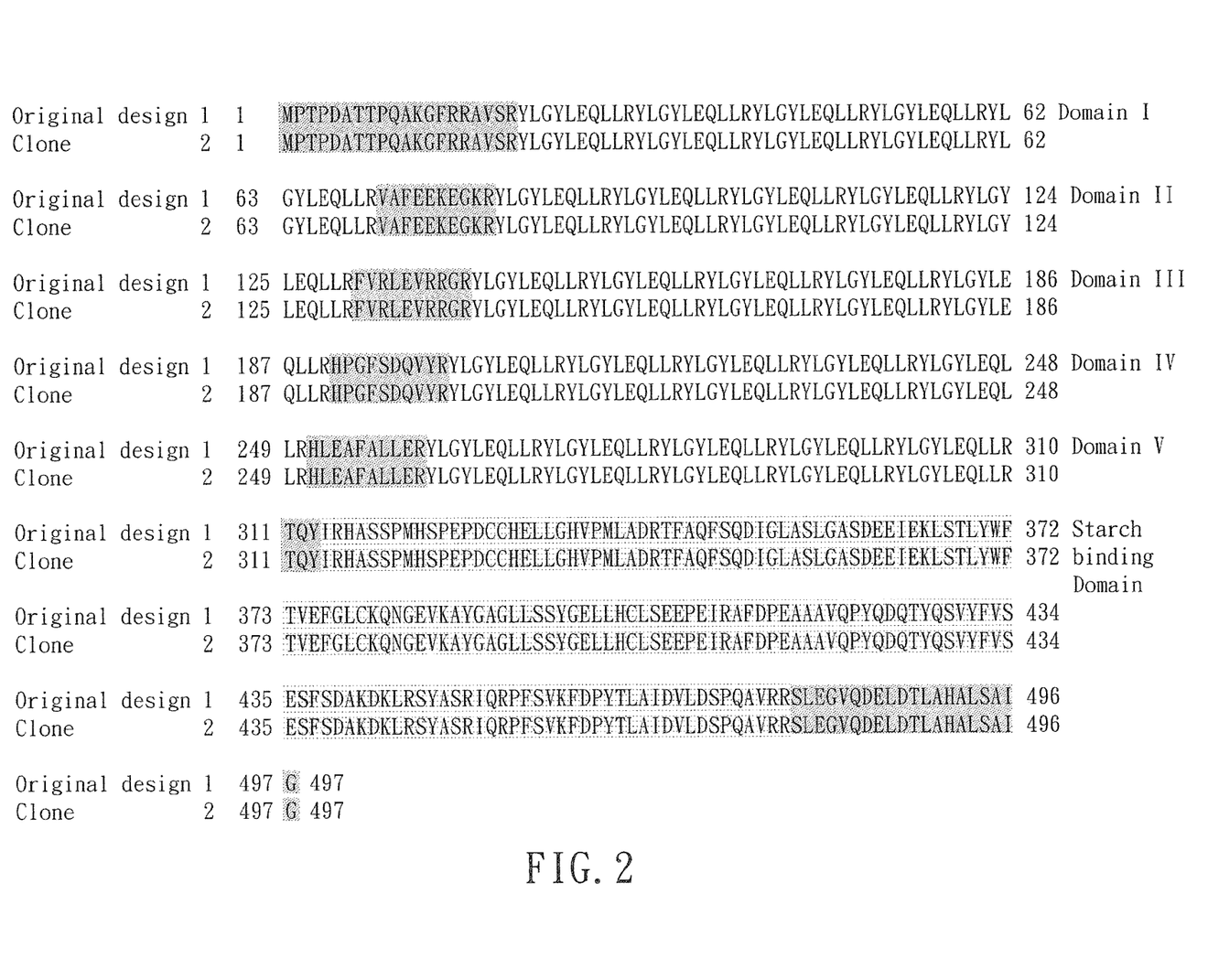
FIG. 2 is sequencing result demonstrating human tyrosine hydroxylase with the sleep-inducing peptide YLGYLEQLLR reconstitute, wherein the white regions are consecutively multiple copies of the sleep-inducing peptide reconstituted in five replacement regions, the gray regions are the original regions in human tyrosine hydroxylase and the light gray region is starch binding domain.

The sequencing result in FIG. 2 shows the sleep-inducing peptide YLGYLEQLLR which was substituted into the HTH. There were 314 amino acids in five replacement regions substituted by the DNA sequence encoding said sleep-inducing peptide. The final recombinant protein product contains 5 sets of 5 consecutively copies of sleep-inducing peptides and to sum up 25 sleep-inducing peptides in a protein of final recombinant protein product. Moreover, above mentioned method has been also utilized for synthesizing the DNA sequence encoding the consecutively multiple copies bioactive peptides such as hyperglycemia-reducing peptides CDALQEIAR (SEQ ID NO: 3) and hypertriglyceride-reducing peptide VVYP (SEQ ID NO: 4).

2. Protection of the Bioactive Peptide

Figure 4:
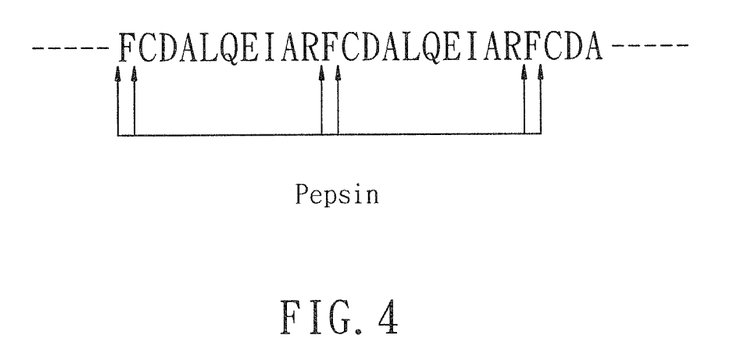
FIG. 4 is demonstrating the pepsin cutting sites within the bioactive peptide CDALQEIAR.

We also find that pepsin, an endopeptidase, specifically cuts N-terminal and C-terminal ends of the phenylalanine (F) within the peptide chain while they are taken into the digestion tract. Therefore, the hyperglycemia-reducing peptide CDALQEIAR (SEQ ID NO: 5) shown in FIG. 4 is added with the phenylalanine (F) at N-terminal and C-terminal ends to form the amino acid sequence as well as FCDALQEIARF for protecting the functional core region of the peptide, so that consecutively multiple copies of the hyperglycemia-reducing peptide (CDALQEIAR) can be released by pepsin digestion.

Figure 5:
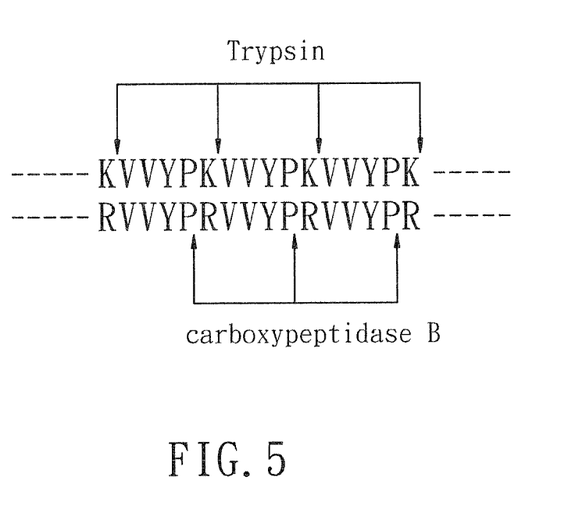
FIG. 5 is demonstrating the trypsin and carboxypeptide B cutting sites within the bioactive peptide VVYP.

Furthermore, trypsin is the endopeptidase existed in small intestine for cutting peptide bonds at the C-terminal of arginine (R) or lysine (K). FIG. 5 shows the example of modified hypertriglyceride-reducing peptide K/R VVYP K/R which is composed of the functional hypertriglyceride-reducing peptide VVYP and the additional lysine or arginine at both N-terminal and C-terminal end of functional core region. In small intestine, the secreted trypsin will digest the peptide bond of C-terminal of K/R to release multiple copies of functional hypertriglyceride-reducing peptide VVYP K/R. In addition, carboxypeptidase B is another endopeptidase existed in small intestine capable to cut the peptide bond at the C-terminal of proline (P). Therefore, the carboxypeptidase B will digest the peptide bond between P and R/K within the peptide VVYP R/K to release the hypertriglyceride-reducing peptide VVYP in small intestine.

Figure 6:
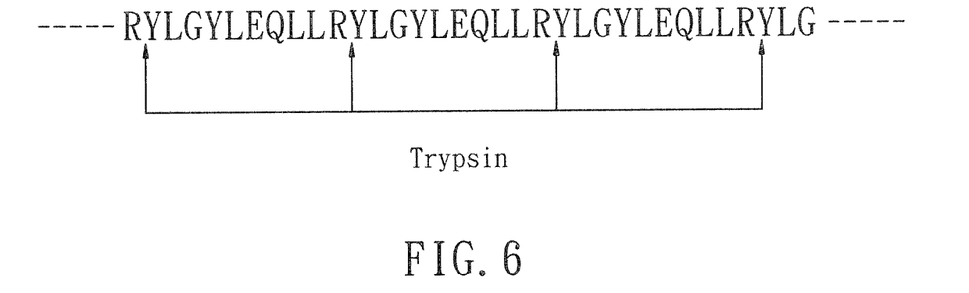
FIG. 6 is demonstrating the trypsin cutting sites within the bioactive peptide YLGYLEQLLR.

FIG. 6 shows the sequence of consecutively multiple copies of sleep-inducing peptides which is composed of functional peptide YLGYLEQLLR with an additional arginine (R) at the N-terminal end to form the amino acid sequence as RYLGYLEQLLR. Therefore, trypsin will cut the peptide bond between R and Y to release multiple copies of YLGYLEQLLR peptides for sleep-inducing. These indicated endopeptidases specifically cut the peptide bond at the destined position to release the functional peptides and that is accurate, effective and reliable.

Example 3

Transformation and Expression of the Peptide-Protein

After replacing consecutively multiple copies of the bioactive peptide into the carrier protein, the expression plasmid is transformed into the biosafety, edible and endotoxin-free strain of yeast (*Yarrowia lipolytica*) by YLEX expression kit (Yeastern Biotech Co., Ltd., Taiwan). Wherein, the transformed DNA sequence encoding the recombinant peptide-protein is targeted into 5S-rRNA loci.

According to the experiment result, there are 82 sets of the recombinant peptide-protein inserted into 5s-RNA loci in single yeast. Therefore, a transformed yeast is capable to produce 3280 peptide-proteins that is calculated from 40 times 82. Actually, the minimal amount of peptide-protein acquired from 1 L yeast fermentation medium is 200 grams and 60% of said produced peptide-protein is the bioactive peptides. The result suggests that there are 120 grams of the bioactive peptide in 200 grams of the peptide-protein acquired from 1 L fermentation.

Figure 3:
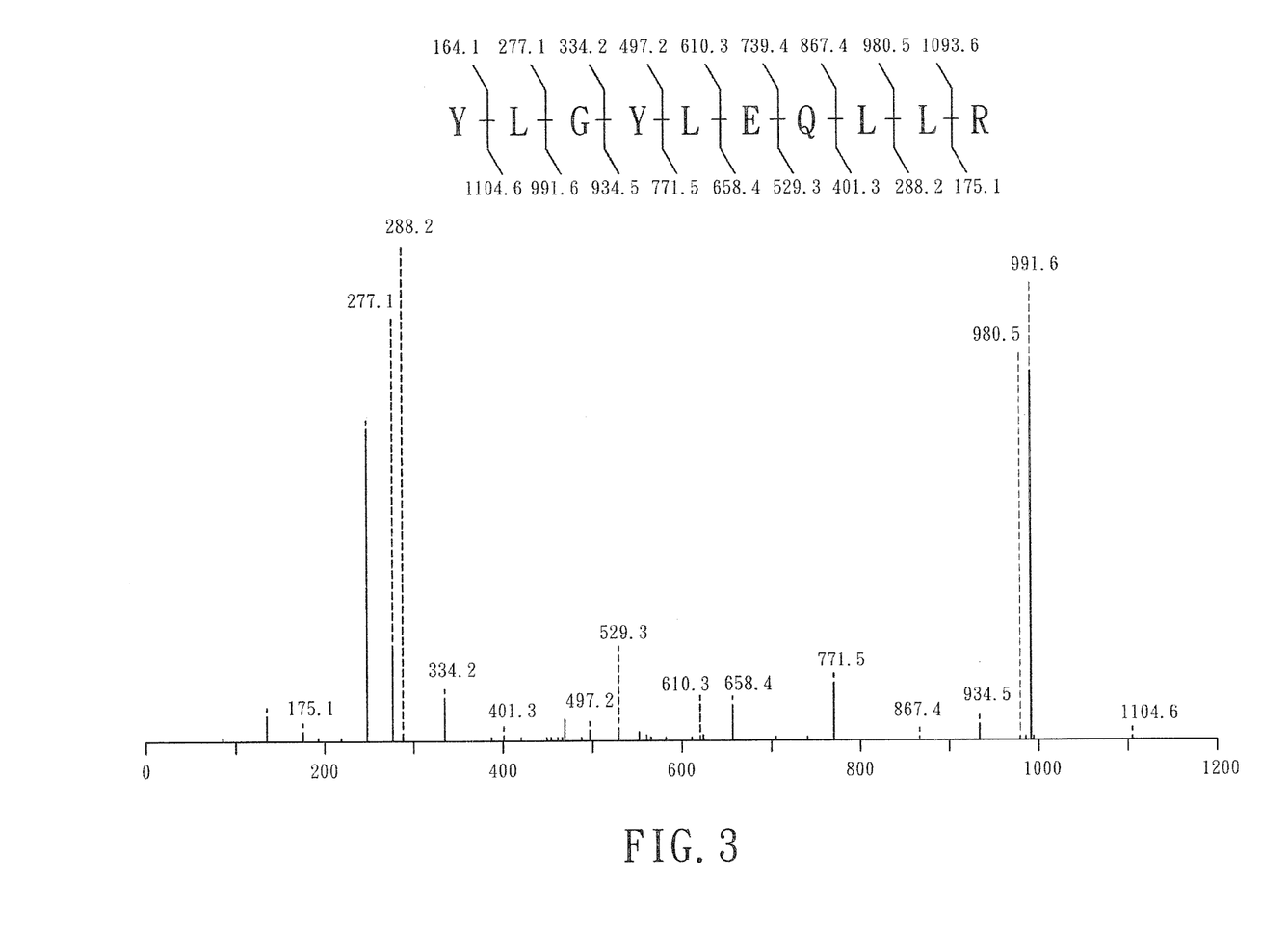
FIG. 3 is amino acid sequence of the bioactive peptide determined by LC-MS-MS.

The produced recombinant protein containing the sleep-inducing peptide is confirmed by LC-MS-MS after digested by trypsin and the result is showed as YLGYLEQLLR in FIG. 3. This sleep-inducing peptide within the recombinant protein is protected from the enzymatic abolishment in oral cavity, esophagus and stomach and the peptide is digested by trypsin to release in small intestine, to be absorbed and to express its bioactive function.

The amino acid sequences of the other bioactive peptides, including hyperglycemia-reducing peptides CDALQEIAR and hypertriglyceride-reducing peptide VVYP can also be confirmed by LC-MS-MS.

According to above mentioned experiment design and method in this invention, the peptide-protein can be produced by this way, and it reveals that 200 gram of the peptide-protein are acquired from 1 liter of fermentation medium mixture after the purification through starch binding. Furthermore, the bioactive peptides are protected by the carrier protein to release in duodenum and small intestine, and to be absorbed and to express its bioactive function. Unlike the prior art of unprotected peptide which needs to take 200~300 mg each day and has no instant effect. The reason of the poor efficacy of the unprotected peptide lies on exopeptidase degradation or acid environment abolishment in oral cavity, stomach and small intestine. Therefore, the amount of the unprotected peptide absorbed by duodenum or small intestine is too rare to achieve the claimed functions. This is the advantage of the peptide-protein produced from this invention compared of the prior art.

Figure 7:
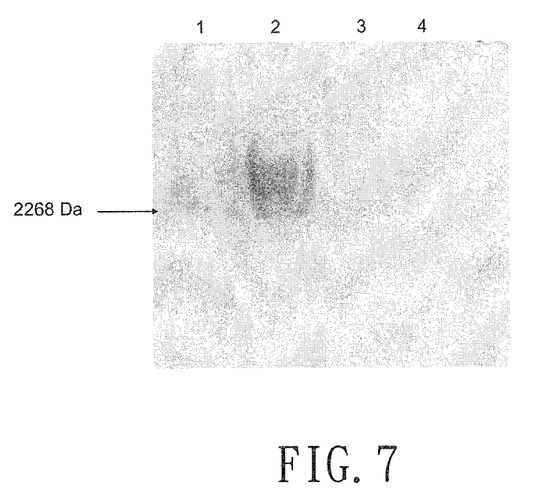
FIG. 7 is SDS-PAGE electrophoresis result demonstrating incubation of protected sleep-inducing peptide YLGYLEQLLR and unprotected sleep-inducing peptide with saliva, gastric juice and intestinal juice. Lanes 1&2 are the protected peptide-protein and lanes 3&4 are the unprotected peptide. Lane 2&4 are the peptides incubated with saliva, gastric juice and intestinal juice.

The equal amount of the peptide-protein containing the bioactive peptide YLGYLEQLLR and the unprotected peptide respectively and sequentially incubated with saliva for 5 minutes, gastric juice for 30 minutes and intestinal juice for 30 minutes, and then present remnant peptides by SDS-PAGE electrophoresis. FIG. 7 shows that the unprotected peptide is completely absent in SDS-PAGE analysis after the enzyme digestion with saliva, gastric juice and intestinal juice.

Example 4

Biosafety Assay

Biosafety assay is the critical criteria to prove that the peptide-protein can replace the prior unprotected peptide to become a commercial healthy food or protein drug. According the WHO guidance, the acute (5000 mg/kg of rat) and subacute (1000 mg/kg of rat, consecutively administrated for 30 days) toxicity test are orally administrated on the Sprague-Dawley (SD) rats to determine the responses in biochemistry, hematopoietic system and histopathology.

Figure 8:
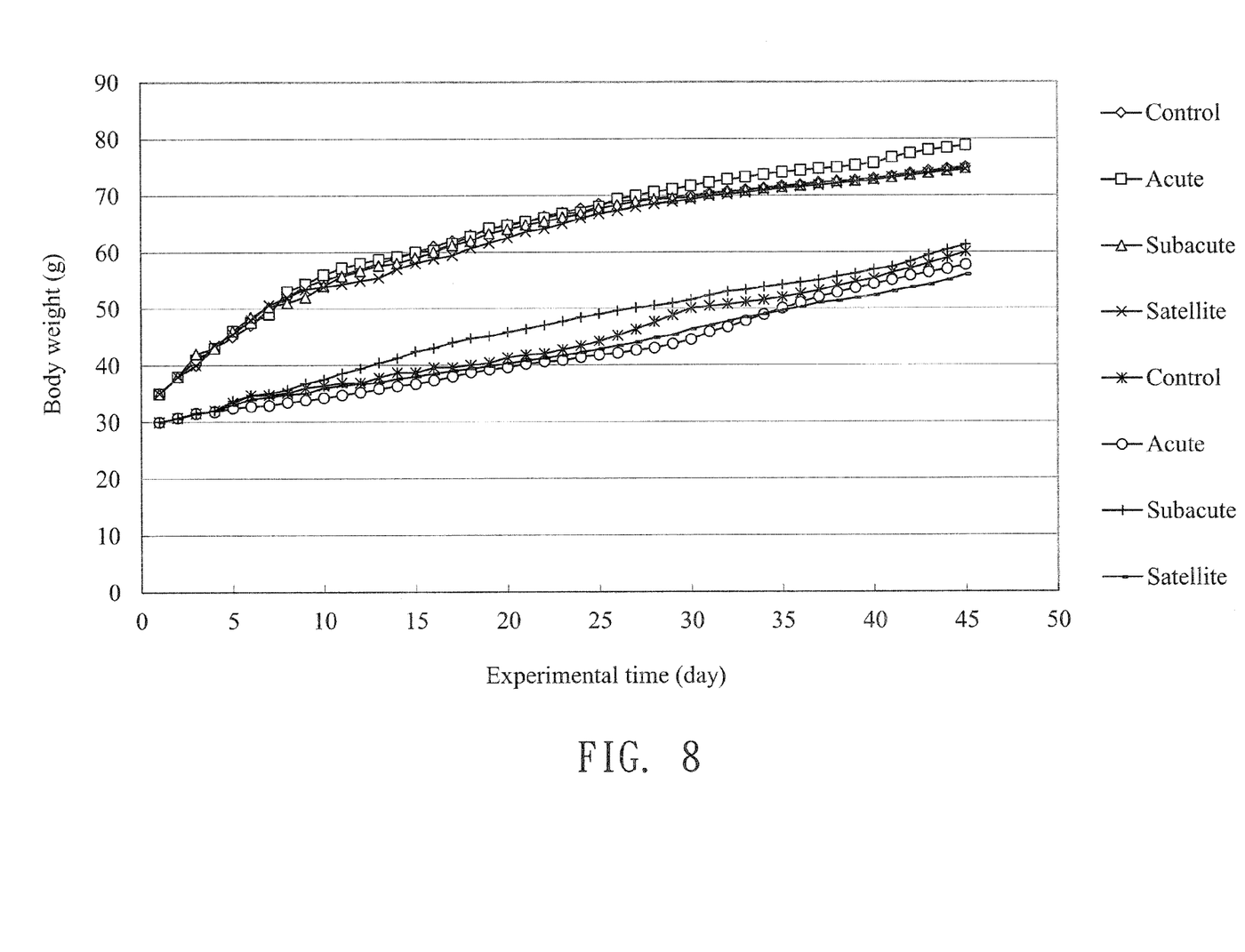
FIG. 8 is growth curve of the SD rats treated with the bioactive peptide produced by the biosynthesis method in this invention. The plots indicated average of body weight at each experimental time. The p value between control group and peptide-protein treated group was calculated by multiple comparison of Dunnett's t-test is less than 0.05.

FIG. 8 shows the growth curve of SD rats after oral administration with the peptide-protein for 45 days. The plots on the growth curve are average of body weight analyzed by ANOVA test. The statistic result analyzed by multiple comparison of Dunnett't-test shows that the experimental group treated with the peptide-protein does not reveal significant difference with the control group.

The results of toxicity tests in Tables 1, 2 and 3 show the treatment of the peptide carried by α-amylase or tyrosine hydroxylase on the SD rats. Neither acute nor subacute toxicity treatments with solid or soluble peptide protein cause toxicity or lethality of the treated rats according to hematology, immunology and biochemistry assays. These results show that the peptide-protein present in this invention reveals biosafety without side effects in the animal test. Therefore, the present peptide-protein is capable of application as pharmaceutical composition.

TABLE 1

Hematological parameters determined from SD rats treated with the peptide-protein present in this invention

| | Female | | | |
|---|---|---|---|---|
| Hematological | Group for subacute toxicity[a] | | Satellite group for subacute toxicity[b] | |
| parameters | Control | Peptide-protein | Control | Peptide-protein |
| RBC ($\times 10^6/\mu l$) | 7.22 ± 0.18 | 7.32 ± 0.51 | 7.12 ± 0.17 | 7.47 ± 0.30 |
| WBC ($\times 10^3/\mu l$) | 8.53 ± 1.51 | 8.09 ± 1.21 | 7.23 ± 0.21 | 7.30 ± 1.33 |
| Hct (%) | 43.96 ± 2.25 | 43.67 ± 3.65 | 45.10 ± 1.37 | 44.73 ± 2.74 |
| Hgb (g/dl) | 43.48 ± 0.93 | 43.52 ± 1.51 | 44.47 ± 0.35 | 44.50 ± 0.87 |
| MCV (fl) | 58.41 ± 1.24 | 56.67 ± 1.44 | 58.90 ± 1.20 | 49.83 ± 1.37 |
| MCH (pg) | 48.22 ± 0.87 | 48.24 ± 0.56 | 49.47 ± 0.65 | 49.33 ± 0.50 |
| MCHC (g/dl) | 31.54 ± 1.57 | 31.11 ± 1.22 | 32.50 ± 1.00 | 32.37 ± 0.21 |
| Platelets ($\times 10^3/\mu l$) | 898.77 ± 49.89 | 845.25 ± 54.32 | 824.77 ± 38.84 | 725.00 ± 41.42 |

| | Male | | | |
|---|---|---|---|---|
| Hematological | Group for subacute toxicity | | Satellite group for subacute toxicity | |
| parameters | Control | Peptide-protein | Control | Peptide-protein |
| RBC ($\times 10^6/\mu l$) | 7.26 ± 0.87 | 7.03 ± 0.73 | 7.99 ± 0.47 | 7.97 ± 0.36 |
| WBC ($\times 10^3/\mu l$) | 11.05 ± 0.88 | 11.25 ± 1.07 | 10.92 ± 0.96 | 10.43 ± 0.21 |
| Hct (%) | 46.76 ± 4.35 | 43.13 ± 3.34 | 47.10 ± 4.49 | 47.24 ± 2.25 |
| Hgb (g/dl) | 44.29 ± 1.03 | 43.89 ± 0.88 | 45.07 ± 0.88 | 44.87 ± 0.23 |
| MCV (fl) | 57.65 ± 1.18 | 57.76 ± 1.23 | 58.85 ± 2.65 | 58.73 ± 1.21 |
| MCH (pg) | 48.10 ± 0.25 | 47.45 ± 0.53 | 48.76 ± 0.16 | 48.51 ± 0.42 |
| MCHC (g/dl) | 31.26 ± 1.65 | 31.05 ± 1.07 | 31.93 ± 1.54 | 31.26 ± 0.24 |
| Platelets ($\times 10^3/\mu l$) | 705.87 ± 61.61 | 721.32 ± 58.67 | 695.30 ± 60.32 | 692.77 ± 60.54 |

Table 1 shows the averages ± S.D. of each hematopoietic parameters determined from 15 rats/group with and without the peptide-protein treatment.
[a]Subacute toxicity group is the hematopoietic parameter results of the rats treated with 1000 mg peptide-protein every day last for 30 days. The rats treated with water are subjected as the control group.
[b]Satellite group for subacute toxicity is the hematopoietic parameter results of the rats examinated after the peptide-protein treatment finished for further 15 days. The difference between the control and the peptide-protein treated rats are calculated by Student's t-test.

TABLE 2

Blood biochemical parameters determined from SD rats treated with the peptide-protein present in this invention

| | Female | | | |
|---|---|---|---|---|
| Blood biochemical | Group for subacute toxicity[a] | | Satellite group for subacute toxicity[b] | |
| parameters | Control | Peptide-protein | Control | Peptide-protein |
| Glucose (mg/dl) | 94.77 ± 13.75 | 89.63 ± 8.12 | 116.43 ± 10.13 | 114.01 ± 9.60 |
| BUN (mg/dl) | 10.47 ± 0.37 | 8.58 ± 0.53 | 13.65 ± 1.32 | 13.30 ± 1.41 |
| Creatinine (mg/dl) | 0.39 ± 0.03 | 0.36 ± 0.02 | 0.38 ± 0.03 | 0.26 ± 0.04 |

TABLE 2-continued

Blood biochemical parameters determined from SD rats treated with the peptide-protein present in this invention

| | | | | |
|---|---|---|---|---|
| Total protein (g/dl) | 6.10 ± 0.14 | 5.28 ± 0.08 | 5.94 ± 0.13 | 5.80 ± 0.11 |
| Albumin (g/dl) | 3.82 ± 0.02 | 3.54 ± 0.17 | 3.83 ± 0.11 | 3.73 ± 0.14 |
| Total bilirubin (mg/dl) | 0.54 ± 0.17 | 0.43 ± 0.05 | 0.59 ± 0.18 | 0.56 ± 0.07 |
| AST(U/l) | 88.43 ± 6.11 | 88.42 ± 6.06 | 91.21 ± 6.87 | 91.03 ± 6.82 |
| ALT(U/l) | 27.35 ± 2.55 | 26.67 ± 2.54 | 30.35 ± 4.13 | 29.95 ± 4.13 |

| | Male | | | |
|---|---|---|---|---|
| | Group for subacute toxicity | | Satellite group for subacute toxicity | |
| Blood biochemical parameters | Control | Peptide-protein | Control | Peptide-protein |
| Glucose (mg/dl) | 102.43 ± 4.97 | 102.01 ± 8.01 | 125.10 ± 6.34 | 118.64 ± 4.02 |
| BUN (mg/dl) | 11.84 ± 0.23 | 7.04 ± 0.31 | 13.47 ± 0.33 | 13.01 ± 0.53 |
| Creatinine (mg/dl) | 0.38 ± 0.07 | 0.31 ± 0.03 | 0.39 ± 0.05 | 0.31 ± 0.02 |
| Total protein (g/dl) | 5.67 ± 0.18 | 5.42 ± 0.21 | 5.85 ± 0.04 | 5.61 ± 0.23 |
| Albumin (g/dl) | 3.63 ± 0.19 | 3.53 ± 0.02 | 3.68 ± 0.13 | 3.54 ± 0.05 |
| Total bilirubin (mg/dl) | 0.49 ± 0.06 | 0.46 ± 0.04 | 0.56 ± 0.07 | 0.46 ± 0.05 |
| AST(U/l) | 98.35 ± 13.12 | 95.07 ± 5.03 | 99.43 ± 6.67 | 96.35 ± 8.11 |
| ALT(U/l) | 35.13 ± 2.63 | 37.32 ± 2.13 | 39.11 ± 2.01 | 41.65 ± 2.56 |

Table 2 shows the averages ± S.D. of each hematopoietic parameters determined from 15 rats/group with and without the peptide-protein treatment.
[a]Subacute toxicity group is the hematopoietic parameter results of the rats treated with 1000 mg peptide-protein every day last for 30 days. The rats treated with water are subjected as the control group.
[b]Satellite group for subacute toxity is the hematopoietic parameter results of the rats exanimated after the peptide-protein treatment finished for further 15 days. The difference between the control and the peptide-protein treated rats are calculated by Student's t-test.

TABLE 3

Histological and immunological parameters determined from SD rats treated with the peptide-protein present in this invention

| | | Female Group for subacute toxicity | | Male Satellite group for subacute toxicity | |
|---|---|---|---|---|---|
| Site | Lesions | Control | Peptide-protein | Control | Peptide-protein |
| Brain | Compression | 2 | 0 | 2 | 0 |
| Pituitary | Hyperplasia | 4 | 1 | 4 | 1 |
| Heart | Mycarditis | 2 | 0 | 0 | 0 |
| Lung | Inflammatory cell foci | 4 | 1 | 3 | 1 |
| Liver | Vacuolation hepatocyte | 8 | 2 | 7 | 2 |
| Stomach | Intestinal metaplasia | 1 | 0 | 0 | 0 |
| Intestine | Diverticulum | 0 | 0 | 1 | 0 |
| Spleen | Increased hematopoiesis | 2 | 0 | 1 | 0 |
| | fibrosis | 2 | 0 | 1 | 0 |
| Kidney | Inflammatory cell foci | 7 | 1 | 4 | 1 |
| Adrenal gland | Hyperplasia and medulla | 2 | 0 | 2 | 0 |
| Urinary bladder | Hyperplasia | 1 | 0 | 1 | 0 |
| Mammary gland | Hyperplasia | 6 | 1 | | |
| Pancreas | Atrophy, islet cell | 6 | 1 | 5 | 1 |
| | Hyperplasia, islet cell | 0 | 0 | 0 | 0 |
| Uterus | Metaplasia | 6 | 1 | | |
| | Hyperplasia | 10 | 1 | | |
| Ovary | Atrophy | 4 | 0 | | |
| Vargina | Cyst, submucosa | 1 | 0 | | |
| Testes | Atrophy, testicular | | | 6 | 1 |
| Prostate gland | Inflammation | | | 1 | 0 |

The number showed in this table suggests the rats with histopathological impairments.

Example 5

Bioactive Test

The above mentioned bioactive peptide-proteins produced from toxin-free, safe and edible yeast expression system in this invention reveal great biological functions, non-toxicity, non-allergic and have no side effect as it shows in Table 4 to Table 7. Furthermore, peptide-proteins which comprise the triglyceride-lowering peptide VVYP, the glycemia-lowering peptide CDALQEIAR or the sleep-inducing peptide YLGYLEQLLR are subjected for functional test, wherein the triglyceride-lowering peptide-protein which reduced 45.3% of triglyceride and 6.3% of body weight within 17 volunteers after one month administration of the peptide-protein.

TABLE 4

The triglyceride-lowing peptide VVYP produced in this invention reveals function in lowing triglyceride in blood, body weight and diastolic pressure of the volunteers

| Tests | triglyceride | | body weight | | diastolic pressure | |
| --- | --- | --- | --- | --- | --- | --- |
| | amount (mg/dl) | percentage (%) | amount (Kg) | percentage (%) | amount (mmHg) | percentage (%) |
| Volunteers | 96 ± 37.3 | 45.3 ± 13.0 | 5.1 ± 1.1 | 63 ± 1.3 | 19.0 ± 9.3 | 21.6 ± 9.3 |

The test of the peptide-protein containing glycemia-lowing peptide CDALQEIAR in 20 volunteers for one month led to reduce glycemia for 35.4% and the consecutive administration of this peptide is capable to maintain the glycemia between 80~100 mg/dl and increase discharge of urine for improving edema in patients.

TABLE 5

The glycemia-lowing peptide CDALQEIAR produced in this invention reveals function in reducing blood glucose of the volunteers

| Tests | blood sugar before eating | |
| --- | --- | --- |
| | amount (mg/dl) | percentage (%) |
| Volunteers | 46.5 ± 5.0 | 35.4 ± 2.5 |

The test of the peptide-protein containing sleep-inducing peptide YLGYLEQLLR in 25 volunteers for one month resolves the problem on delayed sleep and improves sleeping quality. The deep sleep brings the great stamina and pleasure for the volunteer to face the work and challenge in the next day.

TABLE 6

The sleep-inducing peptide YLGYLEQLLR produced in this invention reveals function in the bad sleeping quality of the volunteers

| Test session treatment | D0 | D15 | D30 | D45 |
| --- | --- | --- | --- | --- |
| peptide-protein | 3 | 1*** | 1*** | 1*** |
| (n = 25) | (2-3) | (1-2) | (1-1.5) | (1-1.5) |
| Placebo | 3 | 2 | 1.5 | 1.5 |
| (n = 15) | (2-3) | (1-2) | (1-2) | (1-2) |

Wilcoxson rank test:
**P < 0.01,
***P < 0.005 (vs DO), alpha level is adjusted by Bonferroni inequality calculation.
IQR: interquartile range.

TABLE 7

The sleep-inducing peptide YLGYLEQLLR produced in this invention reveals function in delayed sleep of the volunteers

| Test session treatment | D0 | D15 | D30 | D45 |
| --- | --- | --- | --- | --- |
| peptide-protein | 4 | 1*** | 1*** | 1*** |
| (n = 25) | (1-4) | (1-2) | (1-2) | (1-2) |
| Placebo | 3 | 3 | 2 | 1.5 |
| (n = 15) | (1.5-3) | (1-3) | (0-2) | (1-1.5) |

Wilcoxson rank test:
**P < 0.01,
***P < 0.005 (vs DO), alpha level is adjusted by Bonferroni inequality calculation.
IQR: interquartile range.

Taken together, efficient concentration of the bioactive peptide is the most critical factor to exhibit bioactivity. To insert expression bioactive peptide into carrier protein not only to protect the bioactive peptide from degradation, but also to bring consecutively multiple copies of the bioactive peptides in a single protein molecular (ex: 25 copies) to increase concentration of the peptide. Furthermore, this expression process takes an innovative gene expression system which inserts expression vectors into multiple copies of loci in the chromosome together to extremely elevate the protein amount. This creative and innovative technology to produce the peptide-protein in large scale can make the bioactive peptide become an efficient protein drug in the future.

To sum up, the peptide-protein in this invention is produced from pharmaceutical level process which uses biosafety yeast system. Briefly, consecutively multiple copies of the bioactive peptides are replaced into a carrier protein and then transform the carrier protein into the biosafety and edible yeast strain to produce high concentration of the peptide-protein containing consecutively multiple copies of the bioactive peptide in large scale. This process for biosynthesizing not only can produce the peptide-protein in large scale but also protect the bioactive peptide at the both ends from digestion of exopeptidase and let the bioactive peptide specifically released in duodenum and small intestine to be absorbed through specific digestion and achieve their functions.

For applications in pharmaceutical, the peptide-protein could be emulsion, electuary, gel, lotion, mash, oil soluble concentrate, softener, liposome, nanoparticle, toning lotion, mouthwash, shampoo, milky lotion, spray, suppository, capsule, pastille, powder, syrup, particulate matter, solution, suspension, paste and masking paste for the pharmaceutical applications.

For applications in cosmetic, health care product or health food, the peptide-protein largely produced by present method in this invention can be further processed by pepsin, trypsin or carboxypeptidase B and manufacture as soluble peptides or further add with excipient or food additives to increase addition value and economic benefit.

The above-mentioned specification is only for detailed description with the examples of this present invention and shall not be construed as a scope limitation of this present invention. Any modification or change without departing from the features of this present invention or any equivalent thereof shall be included in the scope of this present invention defined in the following claims.

What I claimed is:

1. A recombinant protein, comprising:
   a human tyrosine hydroxylase according to SEQ ID NO: 1, except that five replacement regions in SEQ ID NO: 1 have each been substituted with polypeptide sequences comprising three consecutive copies of SEQ ID NO: 3;
   wherein said five replacement regions correspond to residues 21-70, 81-130, 141-190, 201-250, and 261-310 of SEQ ID NO: 1.

2. The recombinant protein of claim 1, wherein in each of said polypeptide sequences comprising three consecutive copies of SEQ ID NO: 3, there is a pepsin cutting site between each copy of SEQ ID NO: 3.

3. The recombinant protein of claim 1, wherein in each of said polypeptide sequences comprising three consecutive copies of SEQ ID NO: 3, there is a trypsin cutting site between each copy of SEQ ID NO: 3.

4. The recombinant protein of claim 1, wherein in each of said polypeptide sequences comprising three consecutive copies of SEQ ID NO: 3, there is a carboxypeptidase B cutting site between each copy of SEQ ID NO: 3.

5. The recombinant protein of claim 2, wherein the pepsin cutting site comprises a phenylalanine residue.

6. The recombinant protein of claim 3, wherein the trypsin cutting site comprises at least one selected from the group consisting of an arginine and a lysine residue.

7. The recombinant protein of claim 4, wherein the carboxypeptidase B cutting site comprises a proline residue.

* * * * *

SEQUENCE LISTING

<160> NUMBER OF SEQ ID NOS: 5

<210> SEQ ID NO 1
<211> LENGTH: 497
<212> TYPE: PRT
<213> ORGANISM: Homo sapiens

<400> SEQUENCE: 1

```
Met Pro Thr Pro Asp Ala Thr Thr Pro Gln Ala Lys Gly Phe Arg Arg
 1               5                  10                  15

Ala Val Ser Glu Leu Asp Ala Lys Gln Ala Glu Ala Ile Met Ser Pro
            20                  25                  30

Arg Phe Ile Gly Arg Arg Gln Ser Leu Ile Glu Asp Ala Arg Lys Glu
        35                  40                  45

Arg Glu Ala Ala Val Ala Ala Ala Ala Ala Val Pro Ser Glu Pro
    50                  55                  60

Gly Asp Pro Leu Glu Ala Val Ala Phe Glu Glu Lys Glu Gly Lys Ala
65                  70                  75                  80

Val Leu Asn Leu Leu Phe Ser Pro Arg Ala Thr Lys Pro Ser Ala Leu
                85                  90                  95

Ser Arg Ala Val Lys Val Phe Glu Thr Phe Glu Ala Lys Ile His His
            100                 105                 110

Leu Glu Thr Arg Pro Ala Gln Arg Pro Arg Ala Gly Gly Pro His Leu
        115                 120                 125

Glu Tyr Phe Val Arg Leu Glu Val Arg Arg Gly Asp Leu Ala Ala Leu
    130                 135                 140

Leu Ser Gly Val Arg Gln Val Ser Glu Asp Val Arg Ser Pro Ala Gly
145                 150                 155                 160

Pro Lys Val Pro Trp Phe Pro Arg Lys Val Ser Glu Leu Asp Lys Cys
                165                 170                 175

His His Leu Val Thr Lys Phe Asp Pro Asp Leu Asp Leu Asp His Pro
            180                 185                 190

Gly Phe Ser Asp Gln Val Tyr Arg Gln Arg Arg Lys Leu Ile Ala Glu
        195                 200                 205

Ile Ala Phe Gln Tyr Arg His Gly Asp Pro Ile Pro Arg Val Glu Tyr
    210                 215                 220

Thr Ala Glu Glu Ile Ala Thr Trp Lys Glu Val Tyr Thr Thr Leu Lys
225                 230                 235                 240

Gly Leu Tyr Ala Thr His Ala Cys Gly Glu His Leu Glu Ala Phe Ala
                245                 250                 255

Leu Leu Glu Arg Phe Ser Gly Tyr Arg Glu Asp Asn Ile Pro Gln Leu
            260                 265                 270

Glu Asp Val Ser Arg Phe Leu Lys Glu Arg Thr Gly Phe Gln Leu Arg
        275                 280                 285

Pro Val Ala Gly Leu Leu Ser Ala Arg Asp Phe Leu Ala Ser Leu Ala
    290                 295                 300

Phe Arg Val Phe Gln Cys Thr Gln Tyr Ile Arg His Ala Ser Ser Pro
305                 310                 315                 320

Met His Ser Pro Glu Pro Asp Cys Cys His Glu Leu Leu Gly His Val
                325                 330                 335

Pro Met Leu Ala Asp Arg Thr Phe Ala Gln Phe Ser Gln Asp Ile Gly
            340                 345                 350

Leu Ala Ser Leu Gly Ala Ser Asp Glu Glu Ile Glu Lys Leu Ser Thr
        355                 360                 365
```

```
Leu Tyr Trp Phe Thr Val Glu Phe Gly Leu Cys Lys Gln Asn Gly Glu
    370                 375                 380

Val Lys Ala Tyr Gly Ala Gly Leu Leu Ser Ser Tyr Gly Glu Leu Leu
385                 390                 395                 400

His Cys Leu Ser Glu Glu Pro Glu Ile Arg Ala Phe Asp Pro Glu Ala
                405                 410                 415

Ala Ala Val Gln Pro Tyr Gln Asp Gln Thr Tyr Gln Ser Val Tyr Phe
                420                 425                 430

Val Ser Glu Ser Phe Ser Asp Ala Lys Asp Lys Leu Arg Ser Tyr Ala
                435                 440                 445

Ser Arg Ile Gln Arg Pro Phe Ser Val Lys Phe Asp Pro Tyr Thr Leu
    450                 455                 460

Ala Ile Asp Val Leu Asp Ser Pro Gln Ala Val Arg Arg Ser Leu Glu
465                 470                 475                 480

Gly Val Gln Asp Glu Leu Asp Thr Leu Ala His Ala Leu Ser Ala Ile
                485                 490                 495

Gly

<210> SEQ ID NO 2
<211> LENGTH: 10
<212> TYPE: PRT
<213> ORGANISM: Artificial Sequence
<220> FEATURE:
<223> OTHER INFORMATION: Synthesized peptide

<400> SEQUENCE: 2

Tyr Leu Gly Tyr Leu Glu Gln Leu Leu Arg
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthesized peptide

<400> SEQUENCE: 3

Cys Asp Ala Leu Gln Glu Ile Ala Arg
1               5

<210> SEQ ID NO 4
<211> LENGTH: 4
<212> TYPE: PRT
<213> ORGANISM: Artificial Sequence
<220> FEATURE:
<223> OTHER INFORMATION: Synthesized peptide

<400> SEQUENCE: 4

Val Val Tyr Pro
1

<210> SEQ ID NO 5
<211> LENGTH: 9
<212> TYPE: PRT
<213> ORGANISM: Artificial Sequence
<220> FEATURE:
<223> OTHER INFORMATION: Synthesized peptide

<400> SEQUENCE: 5

Cys Asp Ala Leu Gln Glu Ile Ala Arg
1               5
```